United States Patent [19]

Nakada

[11] Patent Number: 4,888,251
[45] Date of Patent: Dec. 19, 1989

[54] PERSONAL MEMENTO INCLUDING A MILK TOOTH OF A CHILD

[75] Inventor: Akihisa Nakada, Kyouto, Japan
[73] Assignee: Park H. Woo, Osaka, Japan
[21] Appl. No.: 231,059
[22] Filed: Aug. 11, 1988
[51] Int. Cl.$^4$ .................... B44C 5/00; G09F 19/00
[52] U.S. Cl. ........................ 428/542.4; D11/158; D11/162; 428/16; 428/24; 434/263; 434/296
[58] Field of Search .............. 40/538, 409; 433/74; 434/263, 264, 295, , 296, , 386; D11/158, 162; 428/542.4, 24, 16; 272/8 N

[56] References Cited

U.S. PATENT DOCUMENTS

| D. 226,437 | 3/1973 | Jordan et al. | D11/158 |
| D. 293,773 | 1/1988 | Roberts | D11/158 |
| 3,473,247 | 10/1969 | LaFavor et al. | 40/538 |
| 4,231,181 | 11/1980 | Fabricant | 434/264 X |
| 4,238,935 | 12/1980 | Oudet et al. | 63/2 |
| 4,459,110 | 7/1984 | Jackson | 433/74 |
| 4,694,956 | 9/1987 | Sims | 433/229 X |
| 4,717,626 | 1/1988 | Badger | 428/16 X |
| 4,753,024 | 6/1988 | Rinehart | 434/296 X |
| 4,777,745 | 10/1988 | Rose | 428/542.4 X |
| 4,812,127 | 3/1989 | Hernandez | 434/264 |

FOREIGN PATENT DOCUMENTS 3534229 8/1986 Fed. Rep. of Germany ........ 428/13

Primary Examiner—Henry F. Epstein
Attorney, Agent, or Firm—Lowe, Price, LeBlanc, Becker & Shur

[57] ABSTRACT

A personal memento is provided, in which a fallen-off milk tooth is fitted to a decorative article such as an animal toy, an imitation plant, a doll or the like. The milk tooth is incorporated into the overall scope of design of the decorative article to be displayed integral therewith.

10 Claims, 3 Drawing Sheets

PERSONAL MEMENTO INCLUDING A MILK TOOTH OF A CHILD

FIELD OF THE INVENTION

The present invention relates to a personal memento including a milk tooth of a child.

BACKGROUND OF THE PRIOR ART

As is well known, when a child grows normally in the range of 6 to 9 years of age, his milk teeth fall off naturally. The falling-off of a milk tooth is evidence that the child has grown healthily and this event is often memorialized. The first milk tooth that falls off will be one of the incidents in the childhood which is unforgettable, not only for the parents but also for their child.

Due to the fact that the fallen-off milk tooth constituted a part of their child's body they may feel a vague apprehension stealing over them but they may feel regret about discarding it. However, it is often unavoidable that they throw it away because there does not exist any suitable means for preserving it. This means that the parents and the child do not have suitable means for saving it as a valuable article.

SUMMARY OF THE INVENTION

The present invention has been made with the foregoing background in mind, and a principal object is to provide a memory article or memento that includes a fallen-off milk tooth and which also serves the owner of the milk tooth to keep and display it decoratively for a long time.

To accomplish the above object there is proposed according to the present invention a memory article which is characterized in that the fallen-off milk tooth is incorporated as an integral part of the article.

According to the invention, the milk-tooth can be integrated into a variety of decorative articles, e.g., a combination of chicken and imitation egg mounted on a base board, animal toys, dolls, an imitation of a plant or the like, and the milk tooth is correspondingly used in the form of an imitation egg, bell, on the neck of an animal toy, an imitation nose on a toy animal, placement in a display animals mouth, placement on the top of the head of a doll, core of a flower, or the like.

Other objects, features and advantages of the present invention will become readily apparent from reading of the following description which has been prepared in conjunction of the drawings.

DESCRIPTION OF THE PREFERRED EMBODIMENTS

The present invention will be described in a greater detail hereunder with reference to the accompanying drawings which illustrate preferred embodiments thereof.

Figure 1:
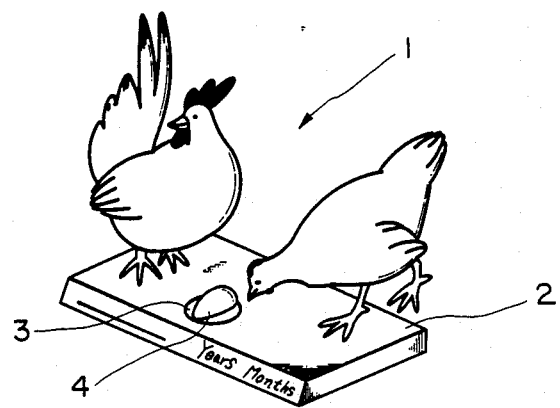
FIG. 1 is a perspective view illustrating the first embodiment of the invention.

First, referring to FIG. 1, in the first embodiment, decorative article 1 includes two chickens fixedly placed on a base board 2. A milk tooth 4 that is to be saved and displayed is immovably placed in a recess 3 formed on an upper surface of the base board 2 with the use of a selected adhesive. As is apparent from the drawing, the age of the child when the milk tooth 4 fell off, his nickname and other data are impressed on the front face of the base board 2. Alternatively, a plate on which the child's age, name and other data are impressed may be adhesively placed there.

The material constituting the decorative article 1, inclusive of the base board 2, may include ceramics, synthetic resin, metal, paper, stone or a combination of the aforesaid and the present invention is not limited to employment of a specific material. This aspect of the present invention also applied to the other embodiments of the invention.

The fallen-off milk tooth 4 should be sufficiently cleaned to remove organic foreign material therefrom before it is immovably placed in the recess 3 on the base board 2. The unnecessary root portion of the milk tooth is cut off as desired. The tooth surface may be ground or colored.

Since the milk tooth 4 is incorporated in the form of an egg in the whole configuration of the decorative article 1, a person who sees the decorative article 1 will not have a negative feeling due to existence of the milk tooth.

The fact that the milk tooth is incorporated within the space as defined by the decorative article also applies to the other embodiments of the invention.

Figure 2:
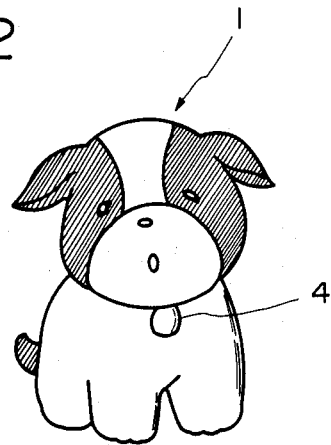
FIG. 2 is a perspective view illustrating the second embodiment of the invention.

FIG. 2 illustrates the case where the decorative article 1 comprises a model of a little dog or a toy dog, and the milk tooth 4 to be memorialized is used as a bell on the neck of the little dog. In this case, the little dog functions as a toy and by fitting the milk tooth thereto it becomes a lovely memorial.

Figure 3:
FIG. 3 is a perspective view illustrating the third embodiment of the invention.
Figure 4:
FIG. 4 is a perspective view illustrating the fourth embodiment of the invention.

FIGS. 3 and 4 illustrate other memorial articles utilizing models. In the case as shown in FIG. 3, the milk tooth 4 is attached to the nose of the model dog, while in the case as shown in FIG. 4 it is placed on top of the head of a doll. Older persons will enjoy seeing such decorative articles because the mementos have traditional charm as memorial items.

Figure 5:
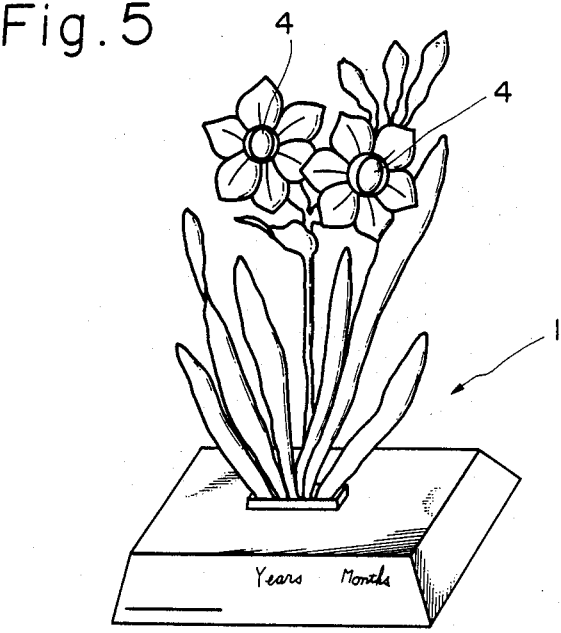
FIG. 5 is a perspective view illustrating the fifth embodiment of the invention.
Figure 6:
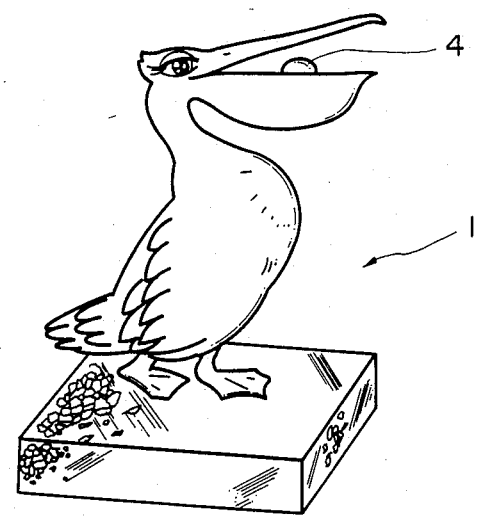
FIG. 6 is a perspective view illustrating the sixth embodiment of the invention.

FIGS. 5 and 6 illustrate examples of other memorial articles having excellent decorative aspects according to this invention. Specifically, FIG. 5 illustrates the case where the milk tooth 4 is located at the core of a daffodil plant model. On the other hand, FIG. 6 illustrates the case where the milk tooth 4 is located in the interior of a mouth of a pelican. As is apparent from the drawing, the pelican takes a posture suggesting that it has obtained a valuable article.

In the case where a decorative article 1 exhibits the configuration of an animal, a plurality of milk teeth to be memorialized may be successively fitted into cavities in the mouth of the animal, e.g., a model of a hippopotamus. Milk teeth may also be used as decorative articles by being integrated into a model of a famous building. With respect to the base board 2, a music box, clock or the like may be employed in place of the flat plates illustrated in the drawings.

A knickknack or model related to the constellation, i.e., astrological sign corresponding to the date of birth of a child whose milk teeth fall off, may also be employed as a memorial article.

While the present invention has been described above with respect to several preferred embodiments thereof, it should of course be understood that it should not be limited only to them but various changes or modifications may be made in any acceptable manner without departure from the spirit and scope of the invention as defined by the appended claims.

What is claimed is:

1. A memory article serving as a personal memento, comprising:
   at least one milk tooth; and
   a decorative article, characterized in that said milk tooth is adhered to be immovably fitted to become an integral part of said decorative article.

2. A memory article as claimed in claim 1, wherein: the decorative article comprises a combination of a chicken and the milk tooth placed to represent an egg, and both the chicken and the milk tooth are placed on a base board.

3. A memory article as claimed in claim 1, wherein: the decorative article comprises an animal toy.

4. A memory article as claimed in claim 3, wherein: a milk tooth is used in the form of a bell which is fitted to the neck portion of the animal toy.

5. A memory article as claimed in claim 3, wherein: the nose of the toy animal comprises a milk tooth.

6. A memory article as defined in claim 3, wherein: a milk tooth is placed in the interior of a mouth of an animal toy.

7. A memory article as claimed in claim 1, wherein: the decorative article comprises a doll.

8. A memory article as defined in claim 7, wherein: a milk tooth is placed on the top of the doll.

9. A memory article as claimed in claim 1, wherein: the decorative article comprises an imitation plant.

10. A memory article as claimed in claim 9, wherein: a milk tooth is fitted into a core cavity of a flower on the imitation plant.

* * * * *